United States Patent [19]
Collier et al.

[11] Patent Number: 4,697,666
[45] Date of Patent: Oct. 6, 1987

[54] SOBRIETY INTERLOCK WITH TIME-LOCKED INTERLOCK MODE

[75] Inventors: Donald W. Collier, Chicago, Ill.; Kip L. Fuller, Denver, Colo.

[73] Assignee: Guardian Interlock Systems, Inc., Denver, Colo.

[21] Appl. No.: 908,036

[22] Filed: Sep. 16, 1986

[51] Int. Cl.$^4$ .............................................. B60R 25/04
[52] U.S. Cl. ........................................ 180/272; 340/53
[58] Field of Search ............... 180/272; 340/52 R, 53; 307/10 R

[56] References Cited

U.S. PATENT DOCUMENTS

| | | | |
|---|---|---|---|
| 3,690,838 | 9/1972 | Luckey | 23/254 R |
| 3,755,776 | 8/1973 | Kotras | 180/272 |
| 3,764,274 | 10/1973 | Collier | 23/255 F |
| 3,780,311 | 12/1973 | Brown | 307/10 R |
| 3,809,067 | 5/1974 | Hoppesch | 128/2 C |
| 3,818,434 | 6/1974 | Gotoh et al. | 73/421.5 R |
| 3,823,601 | 7/1974 | Hoppesch | 73/23 |
| 3,824,537 | 7/1974 | Albertson | 340/53 |
| 3,831,707 | 8/1974 | Takeuchi | 180/99 |
| 3,879,705 | 4/1975 | Binder et al. | 180/272 |
| 4,093,945 | 6/1978 | Collier | 340/279 |
| 4,592,443 | 6/1986 | Simon | 180/272 |

OTHER PUBLICATIONS

Dr. Robert Breakspere, Development of the Lion Analytics VBM Breath Alcohol Activated Interlock, Sep. 17, 1986.

Dr. Ronald Garren, Paper Presented for Presentation at the Workshop on In-Vehicle Alcohol Test Devices, Sep. 17, 1986.

Ms. Patricia L. Zajac, Manufacturers Issues, Sep. 17, 1986.

Primary Examiner—John J. Love
Assistant Examiner—Ross Weaver
Attorney, Agent, or Firm—Wood, Herron & Evans

[57] ABSTRACT

A sobriety interlock for a machine such as a vehicle operates in either an interlock mode or a BYPASS mode. In the INTERLOCK mode, a breath sobriety test must be passed before the machine can be started, while in the BYPASS mode, a breath test is not required to start the machine. When the system is powered up, it operates in the INTERLOCK mode for a predetermined period, preferably about 12 hours before automatically beginning operation in the BYPASS mode. From the BYPASS mode, INTERLOCK mode operation can be selected at any time by actuating a switch which locks in INTERLOCK mode operation for at least the predetermined period of time.

9 Claims, 7 Drawing Figures

SOBRIETY INTERLOCK WITH TIME-LOCKED INTERLOCK MODE

FIELD OF THE INVENTION

The present invention relates to breath sobriety testing. More particularly, the invention relates to an interlock system operable to enable operation of a vehicle such as an automobile or other equipment based on the alcohol content of the breath of a prospective operator.

BACKGROUND OF THE INVENTION

The operation of machines, particularly vehicles by persons under the influence of alcohol is a major safety problem in the United States and many other countries. Despite growing public awareness and government concern, statistics continue to show that a high percentage of automobile accidents causing serious injury or death involve drivers who have been drinking alcoholic beverages in excess. Injuries in the workplace are also often found to be related to the operation of heavy equipment or other machinery by persons impaired by the effects of alcohol.

Various attempts have been made to develop devices which prevent automobiles and the like from being operated by inebriated individuals. Such interlock devices typically operate according to the well known principle that the gas present in the alveoli of the lungs has an alcohol content directly proportional to that of the bloodstream. Blood alcohol content (B.A.C.) thus can be accurately determined by breath testing. A typical breath testing sobriety interlock of this general type is illustrated in U.S. Pat. No. 3,780,311 which shows an alcohol detection circuit connected to a vehicle ignition system to prevent the vehicle from starting if the driver's breath alcohol level exceeds a predetermined limit.

Although sobriety interlock systems are commercially available, they have not been embraced enthusiastically by the driving public as a whole. It is suspected that this reticence is based, at least in part, on a perception that sobriety interlock systems are inconvenient to use. In particular, it is suspected that many drivers believe that it would be unduly burdensome to be required to take and pass a breath sobriety test each and every time they need to start their car when they may only drink on occasion. Such drivers may be discouraged from installing a sobriety interlocking on their vehicle even though they may recognize the hazards of driving while intoxicated and would otherwise welcome the protection afforded by a sobriety interlock system which would prevent them from starting their vehicle if they were intoxicated.

SUMMARY OF THE INVENTION

According to the invention, a sobriety interlock system having a "BYPASS" mode and an "INTERLOCK" mode is provided. In the BYPASS mode, the vehicle can be started without taking or passing a sobriety breath test while in the INTERLOCK mode a sobriety breath test must be passed before the vehicle can be started. When the INTERLOCK mode is selected, it is locked in for a predetermined period of time, preferably twelve hours, which must elapse before BYPASS mode operation resumes. To prevent overriding, the system operates in the INTERLOCK mode on power-up. INTERLOCK mode operation can be selected at any time, however, BYPASS mode resumes only if twelve hours has passed since power-up or the last selection of INTERLOCK mode.

DETAILED DESCRIPTION OF THE INVENTION

Figure 1:
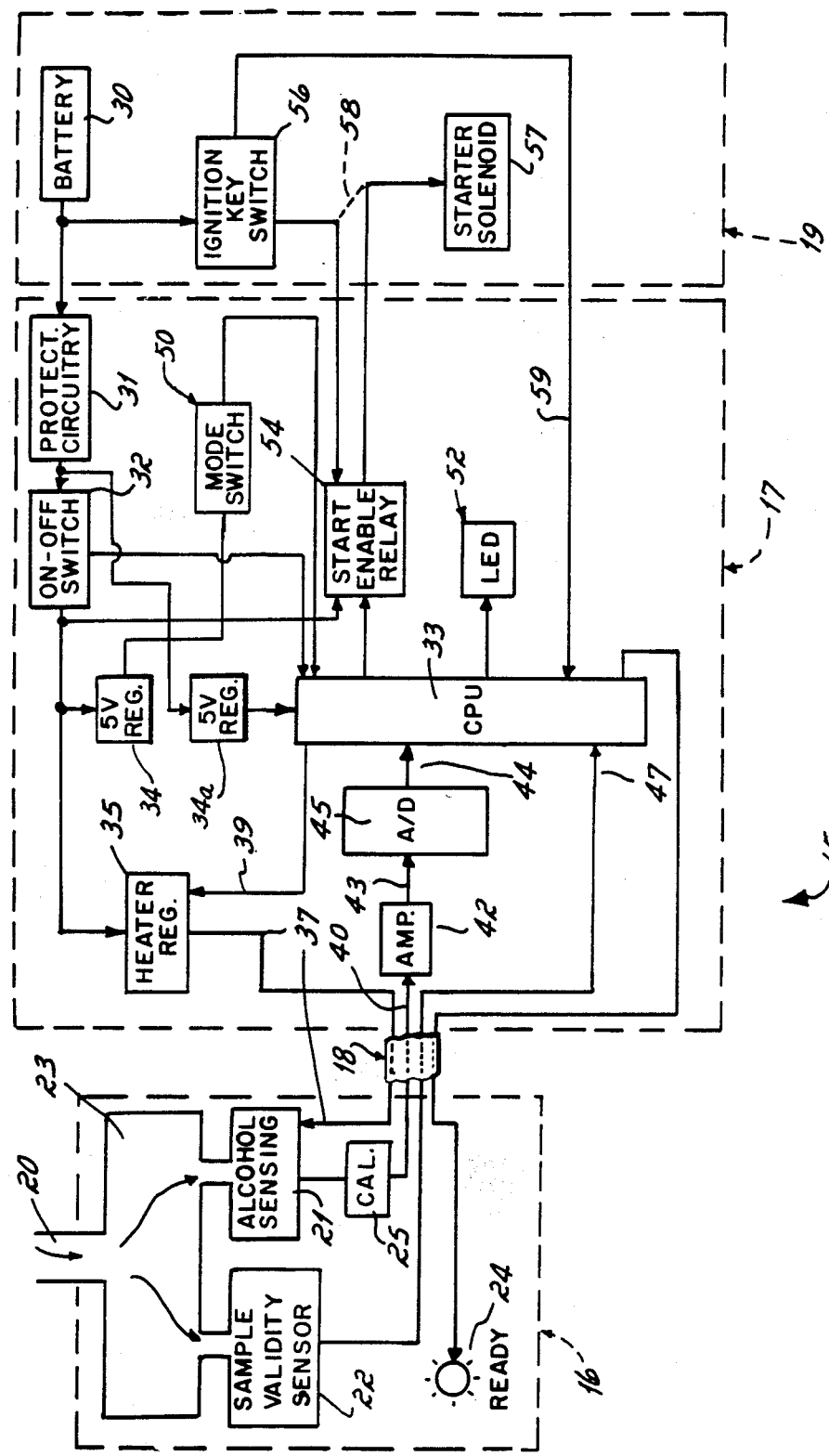
FIG. 1 is a block diagram of a preferred embodiment of a sobriety interlock system embodying the present invention shown connected to a vehicle ignition system.

Referring to FIG. 1, a sobriety interlock 15 embodying the invention includes a remote sampling head 16 connected to a main control module 17 by way of a detachable cable 18. Interlock 15 is connected to a vehicle ignition system 19. According to the invention, interlock 15 operates in one of two alternative modes referred to herein as the BYPASS mode and the INTERLOCK mode. When interlock 15 is in the INTERLOCK mode, the vehicle cannot be started until the prospective driver takes and passes a sobriety breath test based on a breath sample delivered into sampling head 16. On the other hand, when interlock 15 is in the BYPASS mode, the vehicle can be started in the normal fashion without need of taking or passing a sobriety breath test.

Control module 17 is preferably mounted under the dashboard of the vehicle while control cable 18 is of sufficient length to permit sampling head 16 to be removeably fastened to the front or top surface of the dashboard by Velcro or other means in a position readily accessible from the driver's seat. Sampling head 16 includes a breath inlet port 20 which communicates via a manifold 23 with an alcohol sensing device 21 and a sample validity sensor 22. Sampling head 16 also includes a "Ready" LED 24 to indicate when interlock 15 is ready to receive or is in the process of receiving a breath sample. Also contained within sampling head 16 is a calibration potentiometer 25 for calibrating the response of interlock 15 to a particular concentration of alcohol. By detaching cable 18, sampling head 16 is readily disconnected from control module 17 so that sampling head 16 can be removed for replacement, repair or calibration without the necessity of removing control module 17 from the vehicle.

Sobriety interlock 15 is supplied power from vehicle battery 30 through protection circuitry 31 and momentary contact on-off switch 32 which is mounted on the surface of control module 17 in a location accessible to the operator. A central processing unit (C.P.U.) 33 is continuously supplied power from a 5 volt regulator 34a connected to the line side of switch 32. In this way, the memory of C.P.U. 33 can be maintained even when switch 32 has been turned off. A second 5 volt regulator, 34 is connected between the load side of switch 32 and pin T1 of C.P.U. 33. C.P.U. 33 disables vehicle starter solenoid 57 whenever switch 32 is turned off or whenever power is otherwise removed from C.P.U. 33. Switch 32 also supplies power from battery 30 to a low-voltage heater regulator 35 which supplies a variable duty cycle voltage signal 37 to alcohol sensing device 21. The duty cycle of signal 37 is controlled according to the duty cycle of a signal 39 emanating from C.P.U. 33. Alcohol sensing device 21 generates an alcohol sensor signal 40 which is correlated to the alcohol concentration in the breath sample received by device 21 through breath inlet port 20. Alcohol sensor signal 40 is amplified by an amplifier 42 to yield alcohol level signal 43 which is converted to a digital blood alcohol concentration (B.A.C.) signal 44 by an analog to digital (A/D) converter 45. C.P.U. 33 also receives a sample validity signal 47 emanating from sample validity/identity confirmation sensing means 22. A mode switch 50 is connected between the +5 volt supply line of regulator 34 and an input port of C.P.U. 33 to manually select INTERLOCK mode operation as will be explained in further detail below. In the INTERLOCK mode, the prospective operator must pass a breath sobriety test before the vehicle can be started. Interlock 15 is ready for a breath test when "Ready" LED 24 is flashing. To take the test, the operator blows into the sample delivery port 20 of sampling head 16. The response of alcohol sensing device 21 to the alcohol concentration of the breath sample causes B.A.C. signal 44 to assume a value correlated to the blood alcohol concentration of the operation. Provided that signal 47 indicates to C.P.U. 33 that the breath sample is valid (i.e., it is a deep lung sample), B.A.C. signal 44 is compared by C.P.U. 33 with one or more internally stored limit values to determine the result of the test. The breath sobriety test is passed if B.A.C. signal 44 does not exceed a particular limit value. C.P.U. 33 then lights an appropriate one of a group of LED's 52 to inform the operator of the result of the test. If the test has been passed, C.P.U. 33 enables starting of the vehicle by energizing a start enable relay 54 which has been wired between ignition key switch 56 and starter solenoid 57. In the BYPASS mode, C.P.U. 33 keeps start enable relay 54 energized at all times so that the vehicle can be started in the normal fashion by way of ignition key switch 56 without taking a breath sobriety test.

Interlock 15 is installed in the vehicle by connecting protection circuitry 31 to battery 30 and connecting ignition key switch 56 with starter solenoid 57 through a normally open contact of start enable relay 54 after disconnecting line 58 which ordinarily connects key switch 56 with solenoid 57. Ignition key switch 56 is also connected to C.P.U. 33 by way of wire 59 which is energized whenever vehicle ignition switch 56 is in its start or run position.

Figure 2:
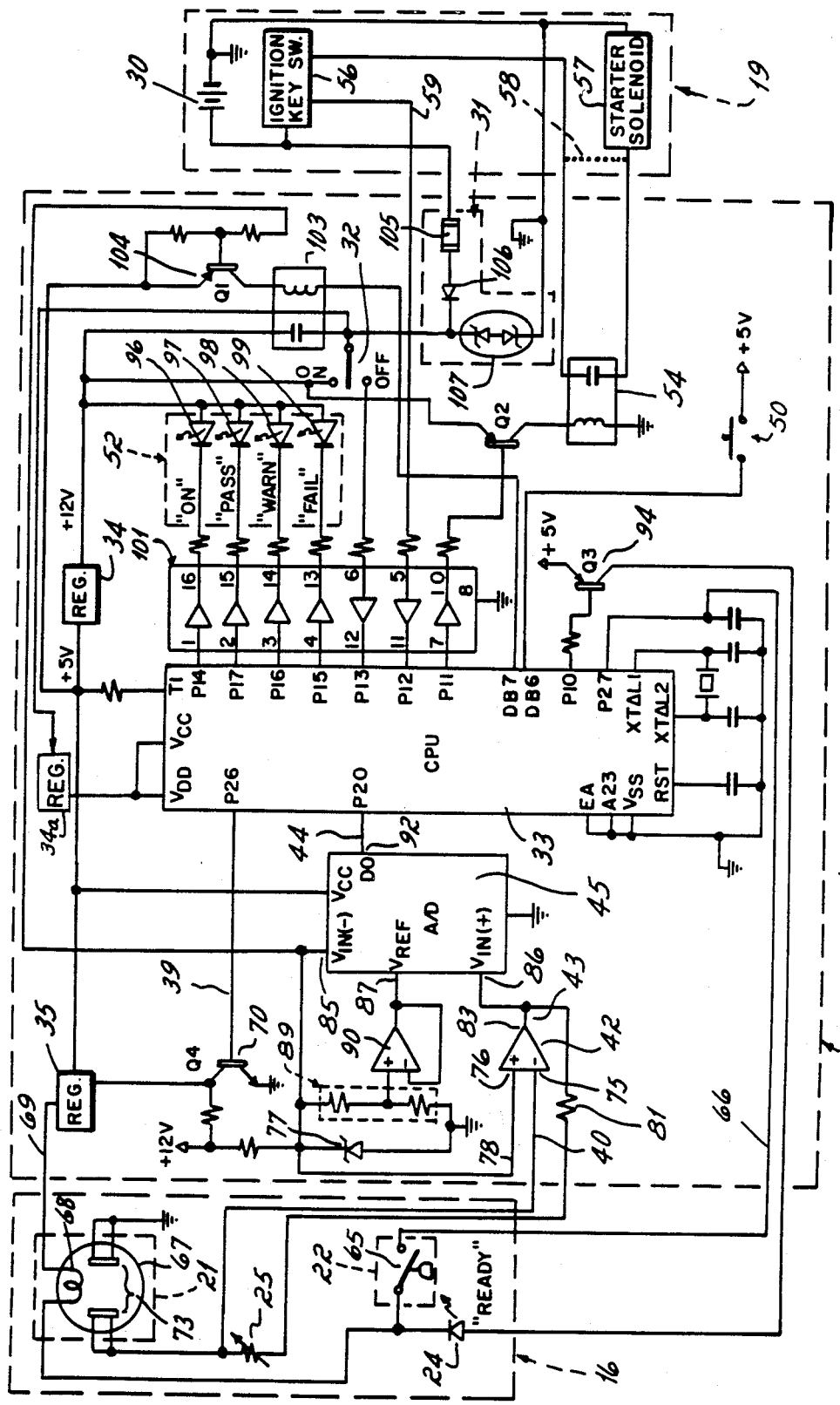
FIG. 2 is an electrical schematic further illustrating the sobriety interlock system shown in FIG. 1.

The sobriety interlock system of FIG. 1 is illustrated in further detail in the electrical schematic of FIG. 2 to which reference is now made and wherein like reference numerals designate like items. Mode switch 50 is preferably a momentary contact, normally open push button switch which is mounted in a location on the surface of control module 17 accessible to the operator. Sample validity sensor 22 is preferably a pressure transducer such as a pressure switch 65, which can be a Fairchild model PSF 100A-3.0, connected to manifold 23 as to respond to the flow of breath through inlet port 20. The state of pressure switch 65 is sensed by C.P.U. 33 at pin P27 by way of line 66. C.P.U. 33 is preferably an Intel Co. part No. 8748 HMOS-E single-component 8-bit microcomputer. Alcohol sensing device 21 may consist of a semiconductor sensor which is preferably model TGS #813 manufactured by Figaro Engineering Company. Alternatively, sensing device 21 may consist of a Model TGS #812, also manufactured by Figaro Engineering Company. Sensor 67 includes a heater 68 which can be energized by way of line 69 by a low voltage heater regulator 35 which is preferably a Texas Instruments type TL497ACN switching voltage regulator. The power delivered to heater 68 is controlled by C.P.U. 33 by outputting an adjustable duty cycle signal 39 from pin P26 to transistor Q4 70 which communicates with regulator 35 by way of line 71 to vary the duty cycle of the output signal of regulator 35 appearing on line 69. Sensor 66 also includes an alcohol sensing element 73 disposed in such a location that at least a portion of the breath sample blown into port 20 will impinge upon its surface. The resistance of element 73 changes in accordance with the alcohol concentration of the breath sample delivered to inlet port 20 to generate alcohol sensor signal 40 received at the inverting input 75 of amplifier 42 which generates alcohol level signal 43. Amplifier 42 is an operational amplifier (OP AMP) whose noninverting input 76 receives a temperature compensated reference voltage from a reference diode 77 by way of line 78. Reference diode 77 is preferably a National Semiconductor type LM336z-25. The gain of OP AMP 42 is determined by a fixed resistor 81 connected in series with calibration potentiometer 25 between the output 83 of amplifier 42 and its inverting input 75. It can be appreciated that fixed resistor 81 and calibration potentiometer 25 can be viewed as a single resistance connected in a voltage dividing relationship with the varying resistance of alcohol sensing element 73. Since OP AMP 42 will tend to maintain the voltage across terminals 75 and 76 at a fixed value and the voltage at noninverting input 76 is held fixed by diode 77, the current through calibration potentiometer and resistor 81 will vary as sensing element 73 varies in resistance with changes in the alcohol concentration of the breath sample. Accordingly, the voltage at the output 83 of OP AMP 42 will vary thereby giving rise to alcohol level signal 43.

The output 83 of OP AMP 42 is connected to the Vin(+) input 86 of A/D converter 45. A/D converter 45 is preferably part number ADC0831 manufactured by National Semiconductor. The Vin (−) input 85 of A/D converter 45 is connected directly to the reference voltage emanating from reference diode 77 while the reference input, Vref 87 of A/D converter 45 receives a fraction of the diode 77 reference voltage by way of voltage divider network 89 and a second amplifier 90. A/D 45 outputs B.A.C. signal 44 from its data out (DO) port to C.P.U. 33 at pin P20. Pin P10 of C.P.U. 33 is connected by way of transistor Q3 94 with "Ready" LED 24. When the interlock 15 is ready to receive a breath sample, C.P.U. 33 causes "Ready" LED 24 to flash. Once pressure switch 65 closes, indicating a breath sample is being received, "Ready" LED 24 stops flashing and remains lighted steadily until pressure switch 65 opens or the validity time is over, whichever occurs first. "Ready" LED 24 is then turned off until the interlock 15 is again prepared to receive a breath sample. LED's 52 comprise an "ON" LED 96, a "PASS" LED 97, a "WARN" LED 98, and a "FAIL" LED 99 each of which is driven under the control of C.P.U. 33 by way of transistor array 101 which is preferably a Sprague type ULN-2003 high-voltage, high-current Darlington transistor array.

After being connected to vehicle ignition system 19 as shown, interlock 15 is activated by moving switch 32 to the "ON" position to supply power from battery 30 to pin T1 of C.P.U. 33 through 5 volt regulator 34. C.P.U. 33 then generates an output signal at pin DB7 to energize a normally open switch relay 103 by way of transistor Q1 104 to latch the power to C.P.U. 33 pin T1 on. "ON" LED 96 remains lighted by C.P.U. 33 by way of pin P14 through transistor array 101 at all times while power is applied to interlock 15. Interlock 15 is deactivated by moving switch 32 to its off position to supply a signal to C.P.U. 33 at pin P13 through transistor array 101 effective to cause C.P.U. 33 to deenergize switch relay 103. The line side of switch 32 is supplied power from battery 30 through protection circuitry 31. Protection circuitry 31 includes a fuse 105 for overcurrent protection, a diode 106 for reverse voltage protection and a bipolar clamp 107 for overvoltage protection.

Sobriety breath testing is based on the well known principle that the gas present in the alveoli of the lungs, located deep within the respiratory tract, has an alcohol content directly proportional to that of the bloodstream. Since breath expired from upper portions of the respiratory tract does not necessarily have an alcohol level proportional to that of the bloodstream, a deep lung sample is essential if interlock 15 is to operate accurately and is not to be defeated by shallow exhalations or a series of short puffs of breath expelled from upper portions of the respiratory tract. Pressure switch 65 serves to insure a "valid" breath sample, which term as used herein refers to a breath sample consisting of a proportion of alveolar gas sufficient to permit an accurate determination of blood alcohol level. Such a breath sample is commonly referred to in the art as a "deep lung" sample of breath.

When in the INTERLOCK mode, interlock 15 insures that breath testing is based on a deep lung breath sample by requiring a breath sample to be delivered to breath inlet port 20 as an essentially continuous, uninterrupted flow sufficient to hold-pressure switch 65 closed for at least a predetermined period of time. C.P.U. 33 monitors the status of pressure switch 65 and aborts the test if pressure switch 65 does not remain closed for at least a predetermined interval of time which is preferably about 4.5 seconds. The switching pressure of pressure switch 65 is selected in accordance with the time pressure switch 65 is required to remain closed during sample delivery (a period referred to herein as the "validity time") and in accordance with the resistance to the flow of breath through the inlet port 20 as to be sufficiently high to insure a deep lung breath sample.

According to the invention, when C.P.U. 33 is initially energized, interlock 15 commences operation in the INTERLOCK mode. In the INTERLOCK mode, a breath sobriety test must be taken and passed before start enable relay 54 is energized thereby permitting the interlocked vehicle to be started. Since INTERLOCK mode operation ensues immediately on initial power-up, INTERLOCK mode operation cannot be avoided by interrupting the power to interlock 15 by momentarily disconnecting battery 30 or cycling on-off switch 32. INTERLOCK mode operation continues for a period of time which is preferably in the range of 8 to 24 hours and most preferably about 12 hours. Assuming mode switch 50 has not been actuated in the preceding 12 hour period, interlock 15 then commences operation in the BYPASS mode. In BYPASS mode, start enable relay 54 is held continuously energized by C.P.U. 33 thereby permitting the vehicle to be started without a breath test.

If mode switch 50 is actuated at any time during BYPASS mode operation, the 12 hour time interval is reset and interlock 15 operates in the INTERLOCK mode for at least the next full 12 hour time period which ensues. Since C.P.U. 33 remains energized continuously by way of regulator 34a regardless of the state of on-off switch 32, timing of the 12 hour interval continues without interruption when the system is de-activated by moving switch 32 to the off position. After the expiration of the 12 hour period following the most recent actuation of mode switch 50, C.P.U. 33 causes interlock 15 to resume BYPASS mode operation by energizing start enable relay 54 continously. Accordingly, there is no need to pass a breath sobriety test to start the vehicle during periods when the driver does not anticipate drinking. However, when an occasion arises when the driver expects to be drinking, the driver can protect himself or herself by actuating mode switch 50 prior to disembarking the vehicle on the way to the occasion thereby causing interlock 15 to lock into the INTERLOCK mode for at least 12 hours. When the operator returns to the vehicle within the 12 hour period, a breath sobriety test must be passed before the vehicle will be able to be started. Thus, the operator, while in full command of his faculties, self-protective instincts and unimparied by alcohol is able to choose whether a breath test should be required at a time in the future when, after imbibing, such sound judgement may not be possible. One can also imagine the sense of security imparted to a parent who actuates mode switch 50 before lending the family car to a teenage driver on Saturday night.

The operation of the invention can be still further understood with reference to the flowchart of FIG. 3 which illustrates the operation of the software program stored in the memory of C.P.U. 33.

Figures 3A, 3B:
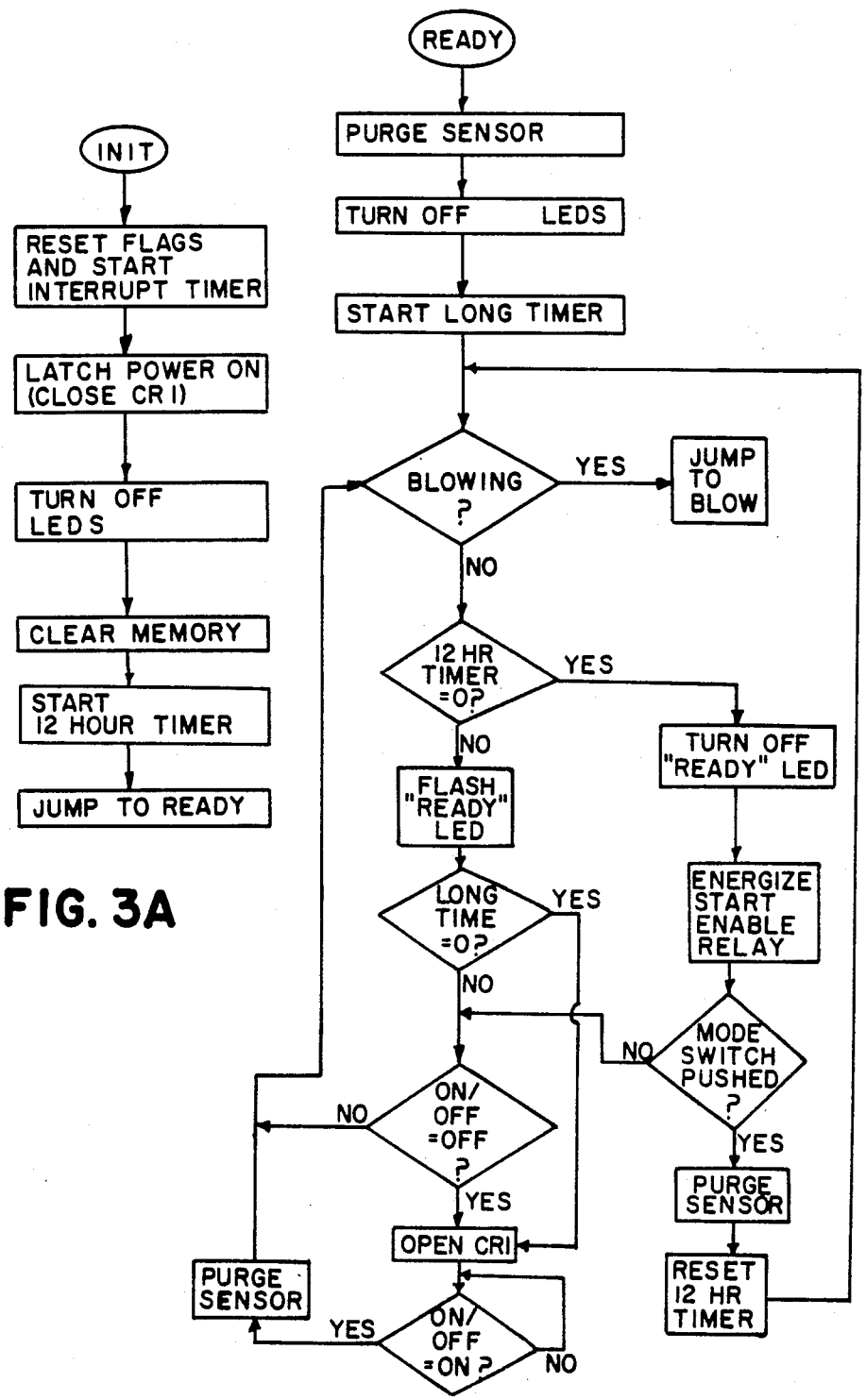
FIG. 3 is a flowchart illustrating the operation of the system of FIGS. 1 and 2.

When C.P.U. 33 is activated for the first time, it begins operation with an initialization routine INIT, the basic steps of which are depicted in FIG. 3A. C.P.U. 33 first resets all internal flags and starts operation of its internal interrupt timer in order to enable C.P.U. 33 to respond to interrupt requests. Next, C.P.U. 33 generates a signal at pin DB7 to energize relay CR1 103 in order to latch power to the system "ON". If any of them are lighted, "PASS", "WARN", and "FAIL" LED's 97, 98, and 99 respectively are switched off. Next, the data memory of C.P.U. 33 is cleared. C.P.U. 33 then starts the 12 hour timer which determines the minimum length of INTERLOCK mode operation and proceeds to the READY subroutine depicted in FIG. 3B to which references is now made.

To prepare alcohol sensor 67 for operation, C.P.U. 33 purges alcohol sensing element 73. The purge sequence begins by causing signal 39 to received at the base of transistor Q4 70 to assume a high duty cycle, thereby causing the low voltage signal on line 69 to likewise assume a high duty cycle. Alcohol sensing element 73 is heated by heater 68 until the surface temperature of element 73 is within the range of 200° C.–400° C. and is preferably in excess of 300° C. This causes any alcohol or other volatile substances to be desorbed from element 73. After the high duty cycle has been maintained for a time sufficient to purge element 73, which is preferably about 40 seconds, C.P.U. 33 reduces the duty cycle of signal 39 as to decrease the temperature of alcohol sensing element 73. The duty cycle of the output of regulator 35 remains at the reduced level until pressure switch 65 closes, thereby indicating commencement of a test, at which time C.P.U. 33 regulates the duty cycle of signal 39 as required to keep sensing element 73 at substantially the same temperature during delivery of a breath sample as existed prior thereto.

Figure 3C:
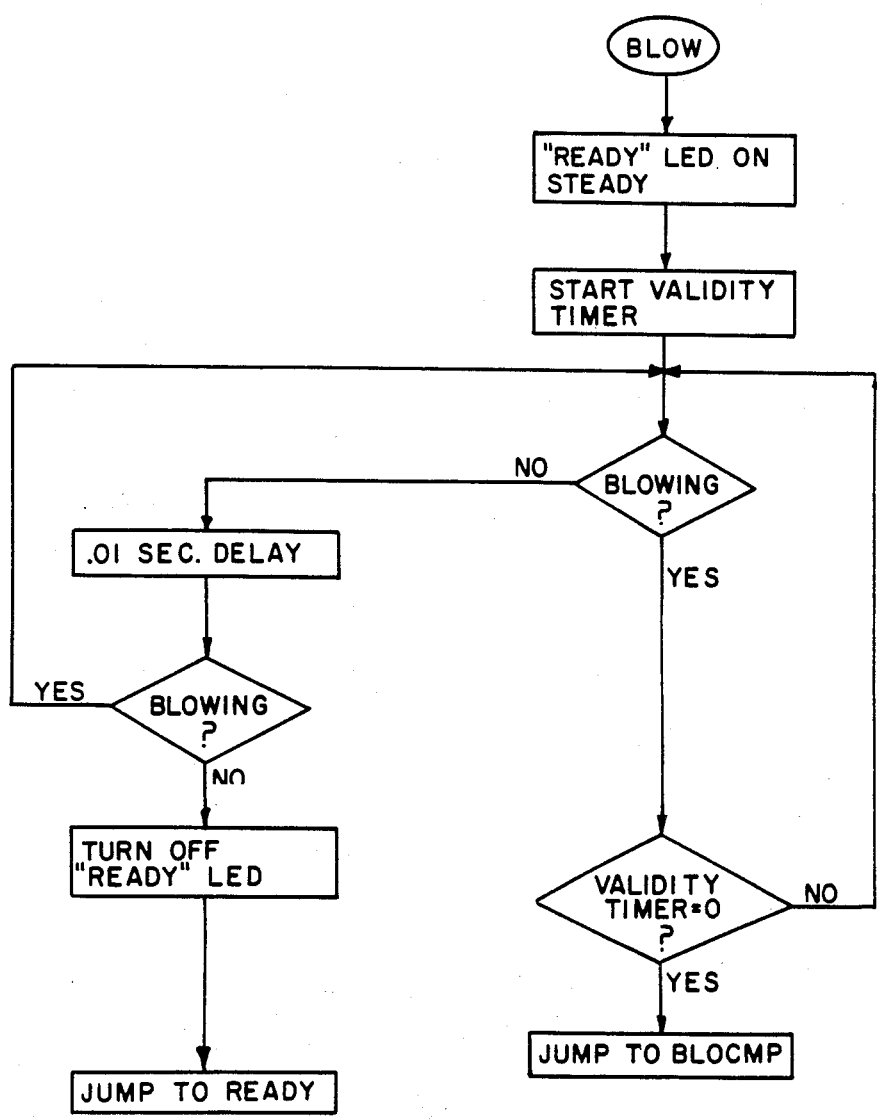
Figure 3D:
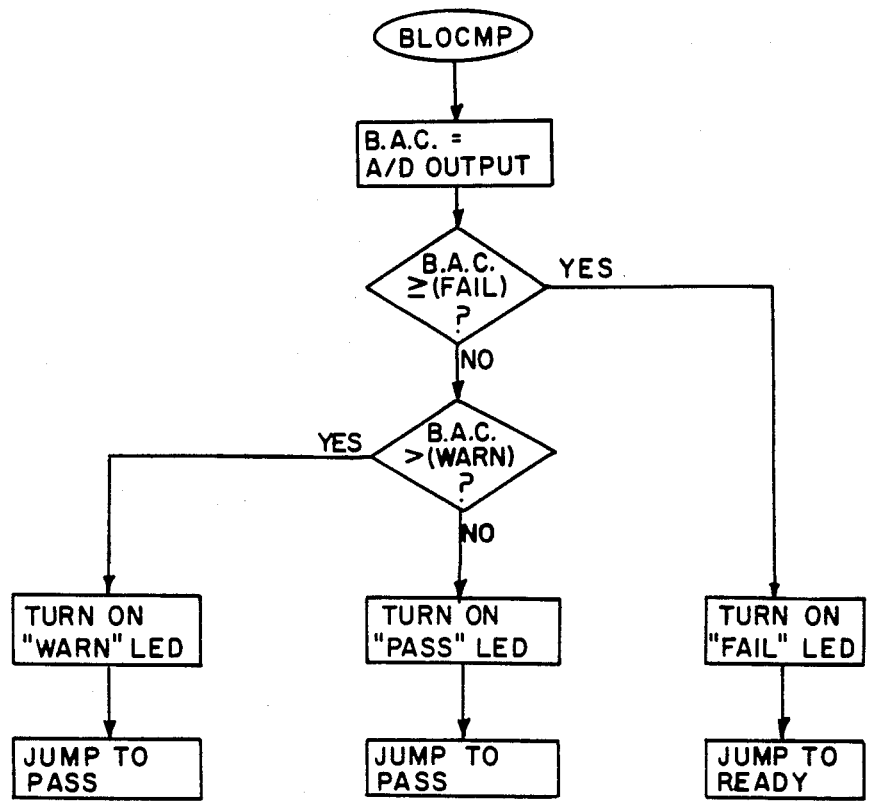

Once the purge sequence is completed, "PASS", "WARN", and "FAIL" LED's 97, 98, and 99 respectively are turned off if they have been on. As mentioned previously, "ON" LED 96 is on at all times while interlock 15 is energized. C.P.U. 33 then loads a value designated "LONG TIME" into an internal timer and starts the timer running, counting down from the loaded value to zero. If interlock 15 is not used, as indicated by a closing of pressure switch 65, within the period designated "LONG TIME", which is preferably on the order of 14 hours, interlock 15 is deactivated by opening relay CRI 103 to conserve vehicle battery 30. When relay 103 is deenergized, it can be appreciated that the vehicle will be unable to be started. This is so because start enable relay 54 is driven by transistor Q2 whose emitter wired to the on terminal of on-off switch 32. Unless switch 32 is in the on position or relay CR1 103 is energized, Q2 is incapable of energizing start enable relay 54. C.P.U. 33 repeatedly checks the status of the 12 hour timer. If the 12 hour timer has not timed out, C.P.U. 33 continuously interrogates the status of pressure switch 65 by way of pin P27 until the "LONG TIME" period ends. When the 12 hour timer is running, C.P.U. 33 flashes "Ready" LED 24 to indicate that interlock 15 is operating in the INTERLOCK mode and is ready to receive a breath sample. If C.P.U. 33 senses blowing of a breath sample as indicated by the closing of pressure switch 65 before the "LONG TIME" period is over, the program jumps to a routine designated BLOW as depicted in FIG. 3C and described in further detail below. When the 12 hour timer times out to zero, C.P.U. 33 turns off "Ready" LED 24 to indicate that interlock 15 has begun to operate in the BYPASS mode. If desired, an audible indication of the commencement of BYPASS mode operation can be provided to supplement the visual indication provided by turning on "Ready" LED 24.

When the BYPASS mode is entered, C.P.U. 33 also energizes start enable relay 54 so that starter solenoid 57 can be activated by ignition key switch 56 without first requiring the operator to pass a breath sobriety test. In the BYPASS mode, start enable relay is energized so that interlock 15 has no apparent effect on normal starting of the interlocked vehicle. Once entered, BYPASS mode opeation persists indefinitely until mode switch 50 is pushed or until on-off switch 32 is switched off. So long as neither of those events occurs, C.P.U. 33 keeps start enable relay 54 continuously energized until the "LONG TIME" period is expired. Then, CR1 is deenergized thereby disabling the vehicle as described above.

If mode switch 50 is pushed, the INTERLOCK MODE is entered and alcohol sensor 21 is again prepared for operation by repeating the purge sequence described earlier. After sensor 21 is purged, the 12 hour timer is reset and INTERLOCK mode operation resumes for the next 12 hours. When the "LONG TIME" period expires or, if switch 32 is moved to the off position, C.P.U. 33 opens relay CR1 103 to deactivate interlock 15 to conserve vehicle battery 30. When on-off switch 32 is subsequently moved to the on position, alcohol sensor is prepared for operation by repeating the purge sequence described earlier. When switch 32 is moved to the on position, the 12 hour timer begins timing from the point at which it left off before C.P.U. 33 generated the signal to open relay CR1 103 at the end of the "LONG TIME" period. Thus, the 12 hour timer is not reset at the end of the "LONG TIME" period nor is it reset by deactivating and subsequently reactivating interlock 15 using on-off switch 32. When the 12 hour timer again times out, interlock 15 resumes operation in the BYPASS mode. From the BYPASS mode, the INTERLOCK mode can be entered at any time by actuating mode switch 50. When C.P.U. 33 senses that mode switch 50 has been actuated, it ceases to hold start enable relay 54 continuously energized, purges alcohol sensor 21 and resets the 12 hour timer. INTERLOCK mode operation persists until the 12 hour timer times out, once more at which point BYPASS mode operation resumes.

When the BLOW routine is entered as the result of pressure switch 65 closing, C.P.U. 33 stops flashing "Ready" LED 24 and lights it steadily. When this occurs, C.P.U. 33 sets an internal timer to insure that the flow of breath is continuous and uninterrupted for a period of time sufficient to insure a deep lung sample. This length of time is designated as the "validity time". If pressure switch 65 opens prior to the end of the validity time, thereby indicating that blowing has been interrupted, "Ready" LED 24 is turned off and the program then jumps back to the READY routine. If the flow of breath is sufficient to keep pressure switch 65 closed for the entire length of the validity time, the program then jumps to a "blow complete" routine designated BLOCMP illustrated in FIG. 3D to which reference is now made.

At the end of the validity time, C.P.U. 33 reads B.A.C. signal 44 from the data out (D O) port 92 of A/D converter 45 and compares its magnitude to at least one of two internally stored limits designated (FAIL) and (WARN). The (FAIL) limit is greater than the (WARN) limit and preferably corresponds to the maximum legal blood alcohol content. The (WARN) limit is preferably selected to correspond to a blood alcohol concentration at which most drivers are somewhat impaired but not legally considered incapable of driving. Typically, (FAIL) is selected to correspond to 0.1% blood alcohol concentration while (WARN) is selected to correspond to 0.05% blood alcohol concentration. If B.A.C. signal 44 is greater than or equal to (FAIL), C.P.U. 33 causes (FAIL) LED 99 to be turned on and jumps to the READY routine described above. If B.A.C. signal 44 does not equal or exceed the (FAIL) limit, C.P.U. 33 determines whether the (WARN) limit is exceeded. If so, C.P.U. 33 causes "WARN" LED 98 to turn on and jump to a routine designated PASS which will also be described further below. If B.A.C. signal 44 does not exceed the "WARN" level, "PASS" LED 97 is lighted and the program jumps to the PASS routine.

Figure 3E:
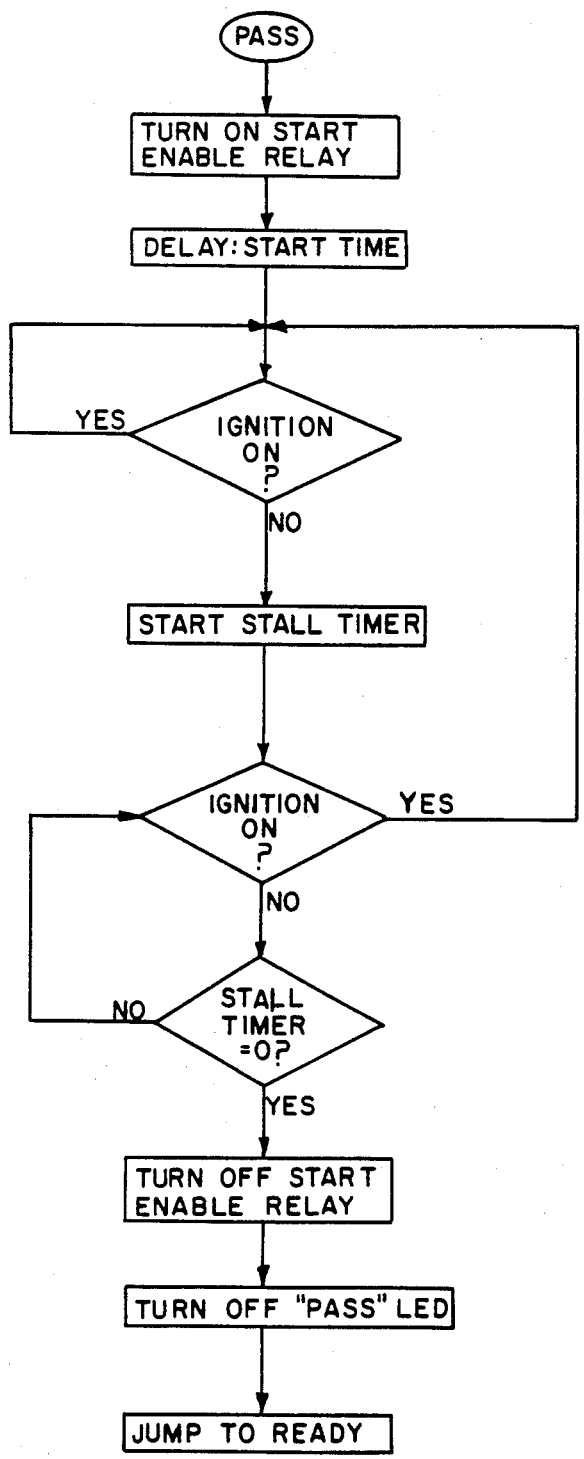

The PASS routine is now described with reference to FIG. 3E. When the PASS routine is entered, start enable relay 54 is energized thereby connecting ignition key switch 56 with starter solenoid 57 as to permit the vehicle to be started. After a breath sobriety test is passed, start enable relay 54 is enabled for a period designated "START TIME" which is preferably 30 to 60 seconds. This deters an operator who has successfully passed a required sobriety test from leaving the vehicle to imbibe. If C.P.U. 33 senses, by way of wire 59, that ignition system 19 is not energized after completion of the "START TIME" delay, the vehicle may have stalled. If the vehicle stalls on a freeway or in another potentially hazardous location, it might be unsafe to require a new test to permit the vehicle to be restarted. Accordingly, C.P.U. 33 starts a "STALL TIMER" which permits the vehicle to be restarted after stalling within a period which is preferably about 30 seconds. If vehicle ignition system 19 is still off at the end of that period, C.P.U. 33 deenergizes start enable relay 54 and turns off "PASS" LED 97 and jumps back to the READY routine thereby requiring a new breath test to be passed before the vehicle may again be started.

While the above description constitutes a preferred embodiment of the apparatus and method of the invention, it is to be understood that the invention is not limited thereby and that in light of the present disclosure of the invention various other alternative embodiments will be apparent to persons skilled in the art. In particular, it should be recognized that while the invention is described with reference to its application to vehicles, many types of machinery can be advantageously equipped with the invention. Also, it should be recognized that the invention can be implemented using means other than an electronic circuit using a central processing unit. For example, satisfactory operation can be obtained using circuitry based on fluidics or electromechanical switching devices such as relays. Accordingly, it is to be understood that changes may be made without departing from the scope of the invention as particularly pointed out and distinctly claimed in the claims set forth below.

I claim:

1. A method of controlling a machine sobriety interlock system of the type operable to disable a machine connected to the interlock unless a prospective operator of the machine passes a breath sobriety test, comprising the steps of:
   (a) sensing the selection of alternative bypass and interlock modes of operation;
   (b) upon sensing selection of said interlock mode, disabling the machine unless a breath sobriety test is passed; and
   (c) upon sensing selection of said bypass mode, permitting the machine to be operated regardless of whether a breath sobriety test is passed, provided that at least a predetermined period of time has elasped since said interlock mode was last selected.

2. The method of claim 1 wherein said predetermined period of time is in the range of 8 to 24 hours.

3. The method of claim 1 further comprising the step of: beginning operation in said interlock mode upon energization of said interlock system.

4. A method of controlling a vehicle sobriety interlock system of the type operable to disable a vehicle connected to the interlock unless a prospective operator of the vehicle passes a breath sobriety test, comprising the steps of:
   (a) sensing the selection of alternative bypass and interlock modes of operation;
   (b) upon sensing selection of said interlock mode, disabling the vehicle unless a breath sobriety test is passed; and
   (c) upon sensing selection of said bypass mode, permitting the vehicle to be operated regardless of whether a breath sobriety test is passed provided that at least a predetermined period of time has elasped since said interlock mode was last selected.

5. The method of claim 4 further comprising the step of: beginning operation in said interlock mode upon energization said interlock system.

6. In a machine sobriety interlock system of the type operable to disable a machine connected to the interlock unless a prospective operator of the machine passes a breath sobriety test, the improvement comprising:
   (a) mode selecting means for selecting alternative bypass and interlock modes of operation;
   (b) means responsive to said mode selecting means for disabling the machine unless a breath sobriety test has been passed when said interlock mode is selected and for permitting the machine to be operated regardless of whether a breath sobriety test is passed when said bypass mode is selected if at least a predetermined period of time has elapsed since said interlock mode was last selected.

7. The apparatus of claim 6 wherein said interlock system begins operation in said interlock mode upon energization of said interlock system.

8. In a vehicle sobriety interlock system of the type operable to disable a vehicle connected to the interlock unless a prospective operator of the vehicle passes a breath sobriety test, the improvement comprising:
   (a) mode selecting means for selecting alternative bypass and interlock modes of operation;
   (b) means responsive to said mode selecting means for disabling the vehicle unless a breath sobriety test has been passed when said interlock mode is selected and for permitting the vehicle to be operated regardless of whether a breath sobriety test is passed when said bypass mode is selected if at least a predetermined period of time has elapsed since the said interlock mode was last selected.

9. The apparatus of claim 8 wherein said interlock system begins operation in said interlock mode upon energization of said interlock system.

* * * * *

UNITED STATES PATENT AND TRADEMARK OFFICE
CERTIFICATE OF CORRECTION

PATENT NO. : 4,697,666

DATED : October 6, 1987

INVENTOR(S) : Donald W. Collier, et al.

It is certified that error appears in the above-identified patent and that said Letters Patent is hereby corrected as shown below:

In the abstract, line 2 - "interlock" should be -- INTERLOCK --

Col. 4, line 18 - "LM336z-25" should be -- LM336Z-25 --

Col. 5, line 32 - "hold-pressure" should be -- hold pressure --

Col. 6, line 2 - "de-activated" should be -- deactivated --

Col. 6, line 20 - "unimparied" should be -- unimpaired --

Col. 6, line 45 - "references" should be -- reference --

Col. 6, line 48 - after "to" and before "received" insert -- be --

Col. 7, line 10 - "CRI" should be -- CR1 --

Col. 7, line 43 - "opeation" should be -- operation --

Col. 7, line 51 - "MODE" should be -- mode --

Col. 9, line 40 - "elasped" should be -- elapsed --

Signed and Sealed this

Twenty-ninth Day of March, 1988

Attest:

DONALD J. QUIGG

*Attesting Officer*  *Commissioner of Patents and Trademarks*